United States Patent [19]
Chapman

[11] 3,957,901
[45] May 18, 1976

[54] INDIRECT HEAT EXCHANGE IN ALKYLATION

[75] Inventor: Charles C. Chapman, Bartlesville, Okla.

[73] Assignee: Phillips Petroleum Company, Bartlesville, Okla.

[22] Filed: Apr. 22, 1974

[21] Appl. No.: 462,877

Related U.S. Application Data

[63] Continuation-in-part of Ser. No. 276,096, July 28, 1972, abandoned.

[52] U.S. Cl. .......................................... 260/683.43
[51] Int. Cl.² ............................................... C07C 3/50
[58] Field of Search ........ 260/683.4, 683.43, 683.48, 260/683.62, 683.49

[56] References Cited
UNITED STATES PATENTS

| | | |
|---|---|---|
| 3,060,116 | 10/1962 | Hardin, Jr. et al. ........... 260/683.4 R |
| 3,548,023 | 12/1970 | Mayhue ........................ 260/683.4 R |
| 3,594,444 | 7/1971 | Jones ............................ 260/683.48 |
| 3,647,905 | 3/1972 | Chapman ..................... 260/683.4 R |
| 3,763,022 | 10/1973 | Chapman ..................... 260/683.48 |

Primary Examiner—Delbert E. Gantz
Assistant Examiner—G. J. Crasanakis

[57] ABSTRACT

A side stream comprising normal butane, isopentane and heavier is withdrawn from the isostripper. This side stream is debutanized and the remaining liquid isopentane and heavier introduced into the liquid alkylate effluent of the isostripper in a controlled manner. The liquid effluent of the isostripper is used to heat another liquid side stream withdrawn from the isostripper and reintroduced into the isostripper.

7 Claims, 2 Drawing Figures

INDIRECT HEAT EXCHANGE IN ALKYLATION

This application is a continuation-in-part of my co-pending application Ser. No. 276,096 filed Jul. 28, 1972, now abandoned.

BACKGROUND OF THE INVENTION

In an alkylation fractionation system, it is desirable that the resultant deisobutanized alkylate product stream have a preselected vapor pressure. In addition, it is desirable that the external heat consumed in the fractionation be as low as possible.

THE INVENTION

It is thus one object of this invention to provide a process for the production of an alkylate.

A further object of this invention consists in the provision of a debutanized alkylate having a controlled vapor pressure.

Still another object of this invention is to provide a process for the production of an alkylate gasoline which process has a low consumption of external energy.

Figure 1:
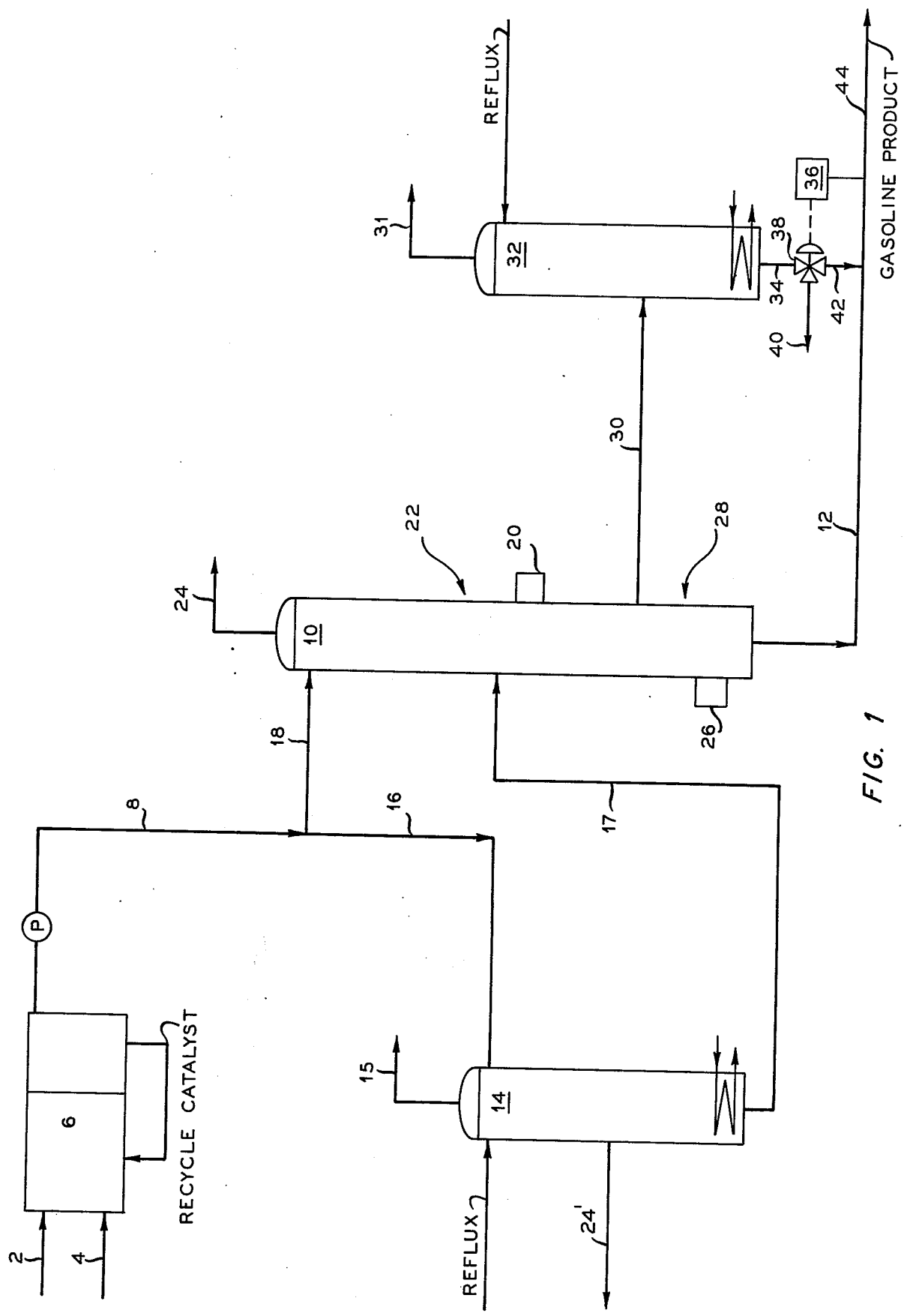
Figure 2:
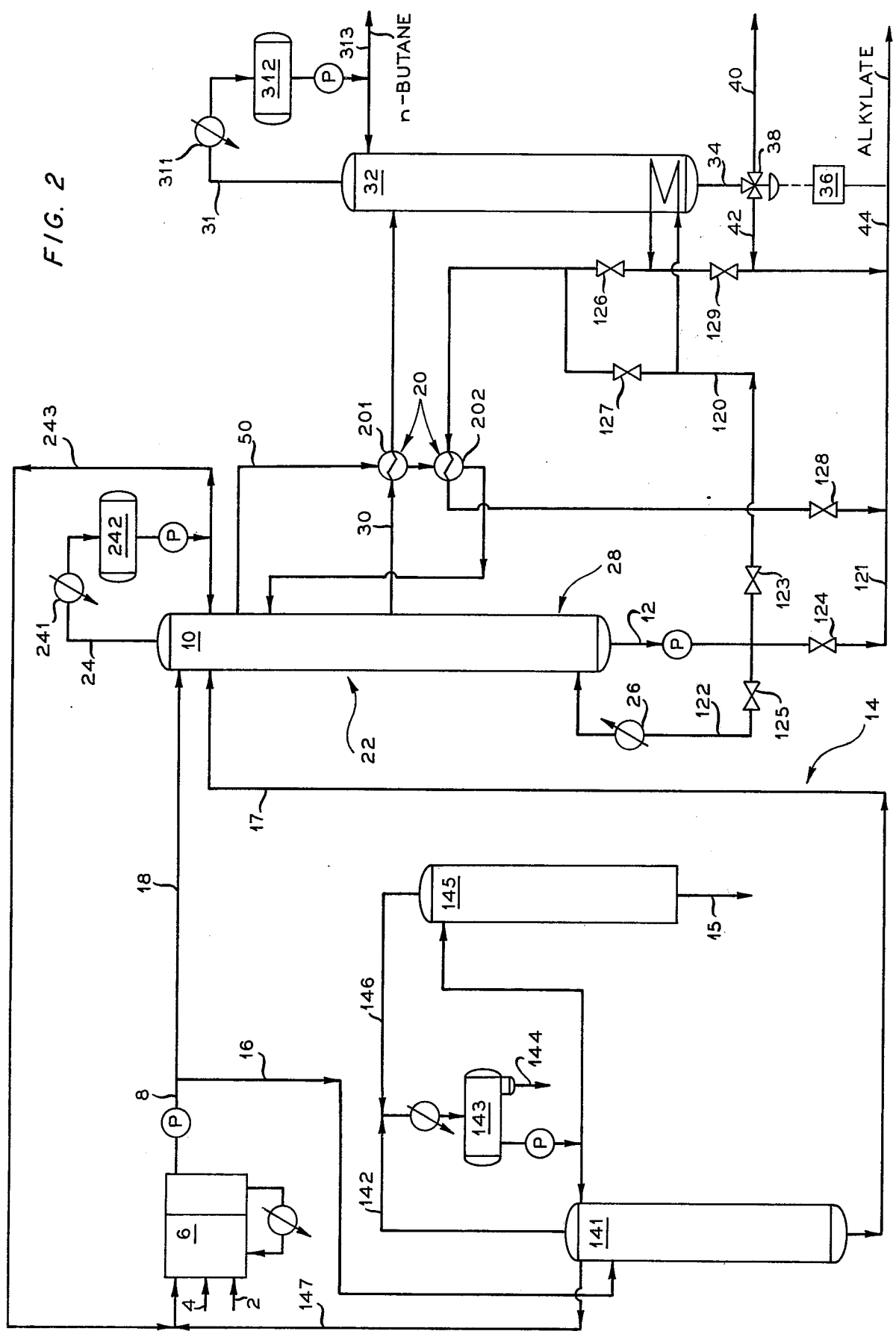

Other aspects, objects and advantages of the present invention will become apparent from the following disclosure of preferred embodiments, the appended claims and the drawing, in which FIG. 1 is a diagrammatic view of an alkylation and fractionation system and FIG. 2 is a diagrammatic view of the system shown in FIG. 1 including additional details.

In accordance with this invention, I have found a process for forming an alkylate product stream having a preselected vapor pressure comprising the steps of introducing an olefin stream and an isobutane stream into a reaction zone, reacting said components in the presence of a catalyst and thus forming a resultant product stream, introducing said product stream into an isobutane stripping zone, separating isobutane from the resultant product stream in said isobutane stripping zone, withdrawing an alkylate product stream from said isobutane stripping zone, withdrawing a side stream comprising normal butane and isopentane vapor from said isobutane stripping zone, introducing said side stream into a debutanizing column, removing normal butane from said side stream in said debutanizing column thus forming a resultant material, and controllably adding the resultant material to the alkylate product stream thus forming an alkylate product stream having a preselected vapor pressure.

In accordance with another embodiment of this invention, there is provided a process for forming an alkylate product stream wherein an olefin stream and an isobutane stream are reacted in the presence of a catalyst, thus forming a resultant product stream, said resultant product stream is introduced into an isobutane stripping zone, a liquid alkylate product stream is withdrawn from said stripping zone, a side stream is withdrawn from an intermediate position of said stripping zone, said side stream is put into heat exchange relationship with at least a portion of said alkylate product stream, the thusly heated side stream is reintroduced into the isobutane stripping zone at a location proximate to its withdrawal.

Further details of this invention will become apparent from the following detailed description of the drawings and the examples.

Referring now to FIG. 1 of the drawing, an olefin feed stream 2 and an isobutane feed stream 4 are passed into and reacted in an alkylation reactor 6 to form a resultant product stream 8. The resultant hydrocarbon product stream 8 is passed into a deisobutanizing zone 10 at which location isobutane 24 for recycle is removed therefrom for forming an alkylate product stream 12, the isobutane being recycled to reactor 6.

The resultant product stream 8 discharging from this reactor 6 can be further processed prior to having isobutane removed therefrom. For example, and as shown in U.S. Pat. No. 3,647,905, the resultant product stream 8 can be split into first and second stream portions 16, 18. The first portion 16 is passed into a depropanizing zone 14 at which location propane is removed via 15 therefrom, and the depropanized resultant product 17 and the second stream portion 18 are passed into the deisobutanizing zone 10, stream 18 functioning also as reflux for column 10. Recycle isobutane is recovered via conduit 24'.

The deisobutanizing zone 10 has a heating zone 20 provided in the middle portion 22 of the zone 10. An isobutane stream 24 is separated therefrom and discharged from the deisobutanizing zone 10 for recycle in the system, for example. A reboiler 26 is associated with a lower portion 28 of the zone 10. The alkylate product stream 12 is discharged from the lower portion 28 of the zone 10 and a stream 30 comprising normal butane vapor rich in isopentane can be removed from a locus near the heating zone 20. Stream 30 can be passed into a debutanizing zone 32 at which location normal butane 31 is separated from the stream 30 and the resultant material 34, comprising isopentane is discharged from the debutanizer and added to the alkylate product stream 12 for controlling the vapor pressure of said stream 12.

It should be understood, however, that the material 34 utilized in this invention for controlling the vapor pressure can be provided by other means.

An analyzer 36 can be associated with the alkylate product stream 12 at a location downstream of the locus at which the resultant material 34 is added for measuring the vapor pressure, delivering a signal in response to that analysis, and controlling the addition of the resultant material 34 in response to the signal by, for example, controlling a three-way control valve 38.

It is desirable to maintain the Reid vapor pressure at a value dependent upon the season and geographic location. In winter, this may be in the range of about 10 to about 14 psi. In the summer, this vapor pressure may be in the range of about 5 to 8 psi. At pressures above about 12 psi, for example, the three-way valve can cause the resultant material 34 to be discharged through line 40 as opposed to passing the material 34 into the stream 12 via line 42. In operation, the valve 38 would generally be throttling and passing material 34 into each of lines 40 and 42.

As is known in the art, it is desirable to maintain the vapor pressure of the product 12 within preselected limits. Product alkylate of desired preselected vapor pressure is removed via 44.

A calculated example of the process of this invention carried out in a system as shown in FIG. 1 is as follows

EXAMPLE I

| | |
|---|---:|
| Olefin Feed (2) (includes propane & butanes) | 35,900 B/I |
| (13% $C_3$=, 28% $C_4$=, 26% isobutane) | |
| Isobutane Feed (4) | 9,800 B/I |
| Recycle Isobutane (24) and (24') | 214,000 B/I |

EXAMPLE I-continued

| | |
|---|---|
| Isobutane from HF Rerun | 5,000 B/D |
| Hydrocarbon Stream (8) | 258,000 B/D |

| Components | Vol. % |
|---|---|
| Propane | 8 |
| Isobutane | 70 |
| Normal Butane | 7 |
| Isopentane (plus) | 15 |
| Total | 100 |

| | |
|---|---|
| Feed to Tower (14) via (16) | 96,800 B/D |
| Feed to Tower (10) via (18) | 161,200 B/D |
| Feed to Tower (10) via (17) | 29,470 B/D |
| Alkylate Yield (12) | 30,150 B/D |
| Reid Vapor Pressure | 6 psi |
| Vapor Feed to Tower (32) via (30) | 4,320 B/D |

| Components | Vol. % |
|---|---|
| Isobutane | 4 |
| Normal Butane | 74 |
| Isopentane (plus) | 22 |
| Total | 100 |

| | |
|---|---|
| LPG Normal Butane (93% nC$_4$) | 2,450 B/D |
| Flow from (42) into Alkylate (12) | 1,910 B/D |

| Components | Vol. % |
|---|---|
| Normal Butane | 2 |
| Isopentane (plus) | 98 |
| Total | 100 |

| | |
|---|---|
| Product Alkylate | 32,060 B/D |
| Reid Vapor Pressure | 7.5 psi |
| Operating Conditions: | |
| Alkylation Zone 6 | |
| Pressure, psi | 130 |
| Temperature, °F. | 90 |
| Depropanizer 14 | |
| Pressure, psi | 285 |
| Temperature, °F. | |
| Top | 126 |
| Bottom | 260 |
| Isobutane Stripper 10 | |
| Pressure, psi | 120 |
| Temperature, °F. | |
| 10 Top | 150 |
| Middle | 170 |
| Bottom | 330 |
| Debutanizer 32 | |
| Pressure, psi | 85 |
| Temperature, °F. | |
| Top | 145 |
| Bottom | 215 |

In FIG. 2 a diagrammatic view of a system for producing an alkylate product stream is shown. The basic elements are the same as in the system shown in FIG. 1. In the following, therefore, only the additional features are described.

The depropanizer system comprises a depropanizing column 141 and an HF stripper 145. The portion 16 of the product stream 8 coming from phase separation zone of the reactor 6 which is to be depropanized is introduced into the depropanizing column 141. The liquid effluent of this column 141 is introduced as stream 17 into the isobutane stripper 10. The gaseous effluent 142 of the depropanizing column 141 containing propane and HF compounds is cooled to a temperature around 100° F. or so, so that the gases liquefy under the existing pressure. The liquefied gases are collected in an accumulator 143. The separate HF liquid portion of this accumulated liquid is withdrawn as stream 144 to be recycled with the HF catalyst into the reactor 6. The hydrocarbon liquid stream is pumped partially into the depropanizing column 141 as reflux and partially into an HF stripper unit 145. The liquid effluent 15 of this HF stripper contains mostly propane whereas the gaseous effluent contains HF and some propane. This gaseous effluent is cooled together with the stream 142 and is introduced into the accumulator 143. A liquid side stream 147 containing isobutane and propane is withdrawn from the upper portion of the depropanizer 141. This stream is reintroduced into reactor 6.

The gaseous effluent 24 coming from the isobutane stripper 10 is cooled at 241 and the liquid formed (mainly isobutane) under existing pressure is collected in an accumulator 242. This liquid is partly pumped as reflux into the isobutane stripper 10 and is partly recycled via 243 into the reactor 6.

From an intermediate position of the isobutane stripper 10 a liquid stream 50 is heated in two heat exchangers 201 and 202. The first heat exchanger utilizes part of the thermal energy of the side stream effluent 30 comprising n-butane and pentane. The larger amount of heat, however, is transferred to stream 50 in the second heat exchanger 202 which utilizes part of the thermal heat of a portion 120 of the liquid effluent 12 of the isobutane stripper 10. The quantity of liquid effluent 120 employed is controlled by a control valve 123. The stream 120 can also serve as a heat source for the reboiling of the debutanizer 32. This heating operation, again, can be accomplished in parallel (valve 126 closed, valve 127 open) or in series (valve 126 open, valve 127 closed) with the heating step in heat exchanger 202. Valves 128 and 129 are provided to shut off the flow of stream 120 through heat exchanger 202 or the heating system of the debutanizer 32.

The liquid effluent 12 of the isobutane stripper 10 can be split up into three streams 120, 121 and 122. Stream 120 serves for the heating operations described above. Stream 121 is part of the alkylate product stream 44. Stream 122 is the portion of the liquid effluent 12 which is recycled and reboiled in reboiler 26 and reintroduced into the isobutane stripper 10. Valves 124 and 125 control the quantity of liquid in streams 121 and 122, respectively. Valve 124 can be closed completely if all the liquid effluent 12 which is not reboiled in reboiler 26 is used for heat exchange purposes in heat exchanger 202 and/or debutanizer 32.

The stream 50 withdrawn at an intermediate position of the isobutane stripper 10 and heated in the heat exchanger 201 and 202 is reintroduced into the isobutane stripper 10 at a location close to the point of its withdrawal, preferably just below this point. The liquid side stream 50 is partly vaporized by the heat exchange operations so that part of this stream when reintroduced into the isobutane stripper 10 moves in upward direction as a vapor, and part of it moves in downward direction as a liquid. Thus, by using the waste heat of the product stream 12, the amount of liquid which otherwise would have to be reboiled in reboiler 26 is considerably reduced.

The gaseous effluent 31 of the debutanizer 32 is cooled at 311 and the liquid formed (mainly n-butane) under the existing pressure is collected in an accumulator 312. This liquid is partly refluxed into the upper portion of debutanizer 32 and is partly withdrawn via line 313.

A calculated example of the process of this invention carried out in a system shown in FIG. 2 is the following:

EXAMPLE II

The figures in parentheses refer to the streams of FIG. 2.

| | | | |
|---|---|---|---|
| (2) | Olefin feed | | 35,870 B/D |
| | volume % $C_3^=$ | 13 | |
| | volume % $C_4^=$ | 22 | |
| | volume % isobutane | 26 | |
| | volume % amylenes | 7 | |
| | volume % isopentane | 18 | |
| | volume % normal butane | 7 | |
| | volume % propane | 7 | |
| | | 100 | |
| (4) | Isobutane feed | | 9,800 B/D |
| (243) | Isobutane recycle | | 156,200 B/D |
| | Isobutane from HF rerun (not shown) | | 3,700 B/D |
| (147) | Iosbutane from depropanizer side draw | | 55,400 B/D |
| | (Note: The isobutane usually comprises 82% of isobutane and 18% of other components.) | | |
| (8) | Hydrocarbon product stream | | 250,200 B/D |
| | volume % propane | 8.5 | |
| | volume % isobutane | 70.0 | |
| | volume % n-butane | 7.0 | |
| | volume % isopentane and heavier | 14.5 | |
| | | 100 | |
| (16) | Hydrocarbon stream to depropanizer | | 89,000 B/D |
| (17) | Hot depropanizer bottoms to isobutane stripper | | 29,470 B/D |
| (18) | Direct stream from reactor to isobutane stripper | | 161,200 B/D |
| (15) | Propane yield | | 3,600 B/D |
| (50) | Liquid side draw from isobutane stripper | | 26,000 B/D |
| | volume % normal butane | 80 | |
| | volume % isobutane | 20 | |
| (30) | Vapor side draw | | 4,320 B/D |
| | volume % normal butane | 53 | |
| | " % isobutane | 3 | |
| | " % isopentane and heavier | 44 | |
| | | 100 | |
| (313) | Normal butane yield | | 2,410 B/D |
| (34) | Isopentane and heavier yield | | 1,910 B/D |
| (120) | Alkylate yield | | 30,150 B/D |
| | 120 (202) alkylate stream into interheater 202 | 24,910 B/D | |
| | 120 (32) alkylate stream to reboiler debutanizer 32 | 5,240 B/D | |
| | (Note: The two streams to heat the interheater 202 and the reboiler of the debutanizer 32 are in parallel.) | | |
| (121) | Direct alkylate product stream | | 0 B/D |
| (42) | Isopentane and heavier stream | | 1,910 B/D |
| | volume % isopentane | 97.5 | |
| | volume % n-butane | 2.5 | |
| (44) | Resulting alkylate product stream | | 32,060 B/D |
| | (Note: All quantities given above are calculated figures and are to be understood as liquid quantities even if the streams partially or totally are vaporous streams.) | | |

Operating conditions

| | |
|---|---|
| Reactor: | 100°F. and pressure to maintain liquid phase. |
| Depropanizer: | Top temperature 134° F. Bottom temperature 263° F. Pressure 300 psig |
| Isobutane stripper: | Top temperature 148° F. Bottom temperature 330° F. Pressure 140 psia |
| Debutanizer: | Top temperature 144° F. Bottom temperature 215° F. Pressure 105 psia |
| Reid vapor pressure of alkylate stream 120 | About 7 psi |
| final alkylate product stream 44: | About 8 psi |
| Temperature of the liquid side draw 50 at the location of withdrawal: | 176° F. |

EXAMPLE II-continued

| | |
|---|---|
| Temperature of the partially vaporized side draw after passing through heat exchangers 201 and 202: | 177° F. |

The temperature of the alkylate stream 120 passing through the interheater 202 changed from about 330° to about 200° F. The temperature of the alkylate stream 120 passing through the debutanizer changed from 330° to 240° F.

The interheating of the liquid side draw 50 by the waste heat of the alkylate stream 120 saves 576 million Btu per day as compared to a process not using the side draw 50 and thus having to reboil this additional material in the isobutane stripper bottom. By using a part of the alkylate product stream 120 to reboil the debutanizer, an additional 81.4 million Btu per day can be saved.

Reasonable variations and modifications can be made, or followed, in view of the foregoing disclosure, without departing from the spirit or scope thereof.

I claim:

1. In the process for forming an alkylate product stream wherein an olefin and isobutane are reacted in the presence of an alkylation catalyst to form a resultant product stream comprising isobutane, n-butane, isopentane, and alkylate, wherein said resultant product stream is introduced into the upper portion of an isobutane stripping zone, wherein an isobutane vapor stream is withdrawn overhead from said isobutane stripping zone, wherein an isobutane liquid side stream is withdrawn from the isobutane stripping zone and wherein an alkylate stream is withdrawn from the bottom of said isobutane stripping zone, the improvement comprising, bringing at least a portion of said alkylate stream into indirect heat exchange relationship with said isobutane liquid side stream, and reintroducing said isobutane liquid side stream to said stripping zone after said indirect heat exchange relationship approximately at the locus of withdrawal of said isobutane liquid side stream from said stripping zone.

2. In a process in accordance with claim 1 wherein a vapor side stream comprising n-butane and isopentane is withdrawn from said isobutane stripping zone, bringing said isobutane liquid side stream into indirect heat exchange relationship with said vapor side stream comprising n-butane and isopentane, and bringing said isobutane liquid side stream, after said indirect heat exchange relationship with said vapor side stream, into indirect heat exchange relationship with at least a portion of said alkylate stream.

3. A process in accordance with claim 1 which includes the steps of withdrawing a vapor side stream comprising n-butane and isopentane from said isobutane stripping zone, removing n-butane from said vapor side stream comprising n-butane and isopentane in a debutanizing zone to provide for an isopentane stream from said debutanizing zone, determining the vapor pressure of said alkylate stream and generating a corresponding signal based on said vapor pressure, adding said isopentane stream from said debutanizing zone to said alkylate stream in response to said corresponding signal to form an alkylate stream having a preselected vapor pressure.

4. A process in accordance with claim 1 wherein said isobutane side stream, after said indirect heat exchange relationship is reintroduced into the isobutane stripping zone at a locus in said zone where the composition of said isobutane liquid side stream is nearly the same as the composition of the materials in the isobutane stripping zone at said locus.

5. A process in accordance with claim 2 wherein said vapor side stream comprising normal butane and isopentane is withdrawn from said isobutane stripping zone at a locus where said vapor does not contain more than 5% isobutane.

6. A process in accordance with claim 3 wherein said alkylate stream is brought into indirect heat exchange relationship with said isopentane stream from said debutanizing zone.

7. A process in accordance with claim 3 wherein said alkylate stream is divided into two alkylate streams, and wherein one of these two streams is brought into indirect heat exchange relationship with said isobutane liquid side stream and the other of these two alkylate streams is brought into indirect heat exchange relationship with said isopentane stream from said debutanizing zone, and wherein said two alkylate streams, ater said indirect heat exchange relationships, are recombined and recovered as at least a portion of the final alkylate product stream.

* * * * *